(12) United States Patent
Banet et al.

(10) Patent No.: US 10,736,523 B2
(45) Date of Patent: Aug. 11, 2020

(54) HANDHELD PHYSIOLOGICAL SENSOR

(71) Applicant: TOSENSE, INC., La Jolla, CA (US)

(72) Inventors: Matthew Banet, San Diego, CA (US); Marshal Singh Dhillon, San Diego, CA (US); Susan Meeks Pede, Encinitas, CA (US); Lauren Nicole Miller Hayward, San Diego, CA (US); Arthur Deptala, Santee, CA (US); Jonas Dean Cochran, Santee, CA (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 319 days.

(21) Appl. No.: 14/988,695

(22) Filed: Jan. 5, 2016

(65) Prior Publication Data
US 2017/0188849 A1    Jul. 6, 2017

(51) Int. Cl.
*A61B 5/0245* (2006.01)
*A61B 5/1455* (2006.01)
(Continued)

(52) U.S. Cl.
CPC .......... *A61B 5/0245* (2013.01); *A61B 5/0205* (2013.01); *A61B 5/02125* (2013.01);
(Continued)

(58) Field of Classification Search
CPC ............ A61B 5/02422; A61B 5/02427; A61B 5/02438
See application file for complete search history.

(56) References Cited

U.S. PATENT DOCUMENTS 5,069,219 A * 12/1991 Knoblich ........... A61B 5/02233
                                                            600/492
5,685,299 A * 11/1997 Diab .................. A61B 5/14551
                                                            356/39
(Continued)

OTHER PUBLICATIONS

Anand et al., Monitoring Changes in Fluid Status With a Wireless Multisensor Monitor: Results From the Fluid Removal During Adherent Renal Monitoring (FARM) Study. Congest Heart Fail. Jan.-Feb. 2012;18(1):32-36.
(Continued)

*Primary Examiner* — Michael R Bloch
(74) *Attorney, Agent, or Firm* — K&L Gates LLP

(57) ABSTRACT

A handheld device measures all vital signs and some hemodynamic parameters from the human body and transmits measured information wirelessly to a web-based system, where the information can be analyzed by a clinician to help diagnose a patient. The system utilizes our discovery that bio-impedance signals used to determine vital signs and hemodynamic parameters can be measured over a conduction pathway extending from the patient's wrist to a location on their thoracic cavity, e.g. their chest or navel. The device's form factor can include re-usable electrode materials to reduce costs. Measurements made by the handheld device, which use the belly button as a 'fiducial' marker, facilitate consistent, daily measurements, thereby reducing positioning errors that reduce accuracy of standard impedance measurements. In this and other ways, the handheld device provides an effective tool for characterizing patients with chronic diseases, such as heart failure, renal disease, and hypertension.

14 Claims, 8 Drawing Sheets

(51) Int. Cl.
   *A61B 5/00*      (2006.01)
   *A61B 5/0205*    (2006.01)
   *A61B 5/0452*    (2006.01)
   *A61B 5/021*     (2006.01)
   *A61B 5/024*     (2006.01)
   *A61B 5/08*      (2006.01)
   *A61B 5/02*      (2006.01)

(52) U.S. Cl.
   CPC ........ *A61B 5/0452* (2013.01); *A61B 5/14551* (2013.01); *A61B 5/4875* (2013.01); *A61B 5/6823* (2013.01); *A61B 5/6825* (2013.01); *A61B 5/0008* (2013.01); *A61B 5/0022* (2013.01); *A61B 5/02028* (2013.01); *A61B 5/02141* (2013.01); *A61B 5/02416* (2013.01); *A61B 5/0809* (2013.01); *A61B 5/4872* (2013.01); *A61B 5/7275* (2013.01); *A61B 5/7282* (2013.01)

(56) References Cited

U.S. PATENT DOCUMENTS

| | | | | |
|---|---|---|---|---|
| 6,336,901 | B1* | 1/2002 | Itonaga | A61B 5/02141 600/499 |
| 6,405,075 | B1* | 6/2002 | Levin | A61B 5/022 600/480 |
| 6,705,990 | B1* | 3/2004 | Gallant | A61B 5/0205 128/903 |
| 7,966,052 | B2* | 6/2011 | DeFusco | A61B 5/0245 600/386 |
| 9,332,941 | B2 | 5/2016 | Banet et al. | |
| 2008/0319327 | A1* | 12/2008 | Banet | A61B 5/0059 600/485 |
| 2014/0236037 | A1 | 8/2014 | Banet et al. | |
| 2016/0106366 | A1 | 4/2016 | Banet et al. | |
| 2016/0235325 | A1* | 8/2016 | Chou | A61B 5/04085 |

OTHER PUBLICATIONS

Harley et al., Pressure-Flow Studies in Man. An Evaluation of the Duration of the Phases of Systole. J Clin Invest. May 1969;48(5):895-905.

Jacques et al., Pulse pressure variation and stroke vol. variation during increased intra-abdominal pressure: an experimental study. Crit Care. 2011;15(1):R33 (9 pages).

Macias et al., Body fat measurement by bioelectrical impedance and air displacement plethysmography: a cross-validation study to design bioelectrical impedance equations in Mexican adults. Nutr J. Aug. 15, 2007;6:18 (7 pages).

Packer et al., Utility of Impedance Cardiography for the Identification of Short-Term Risk of Clinical Decompensation in Stable Patients With Chronic Heart Failure. J Am Coll Cardiol. Jun. 6, 2006;47(11):2245-2252.

* cited by examiner

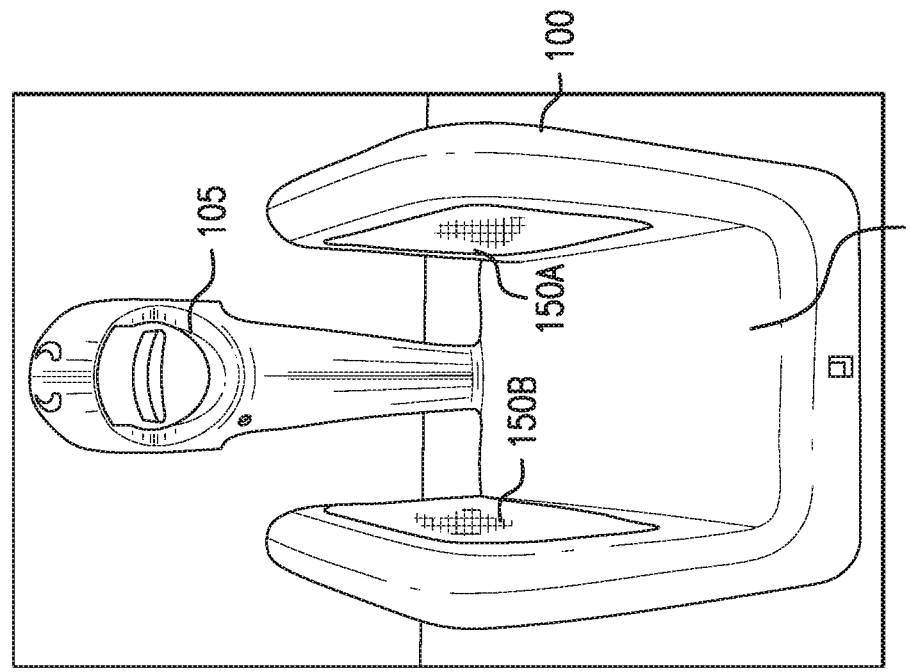
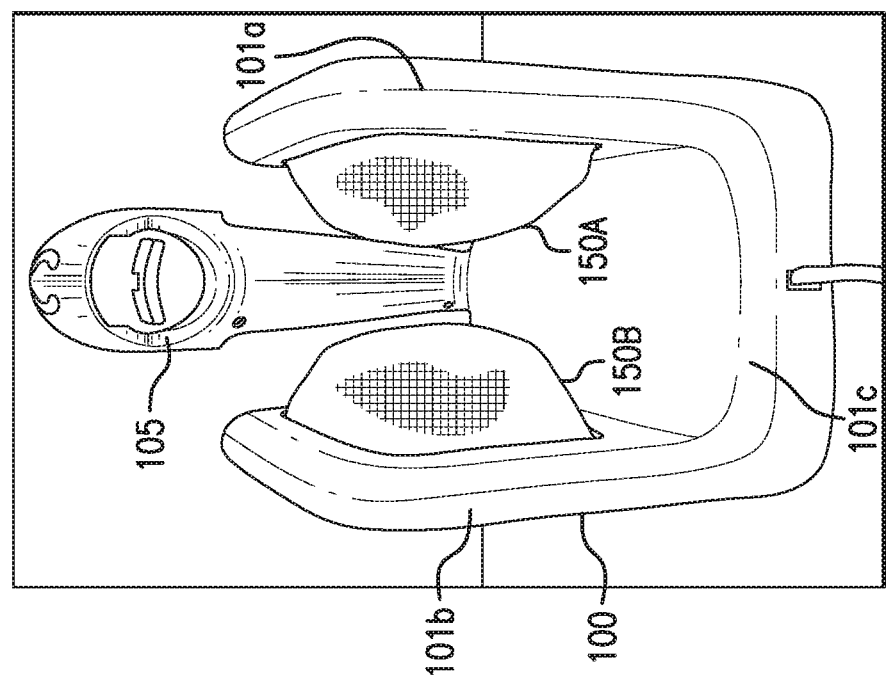

HANDHELD PHYSIOLOGICAL SENSOR

BACKGROUND AND FIELD OF THE INVENTION

1. Field of the Invention

The invention relates to sensors that measure physiological signals from patients, and the use of such sensors.

2. General Background

Physiological sensors, such as vital sign monitors, typically measure signals from a patient to determine time-varying waveforms, e.g. thoracic bio-impedance (TBI), bioreactance (BR), and electrocardiogram (ECG) waveforms, with electrodes that attach to the patient's skin. These waveforms can be processed/analyzed to extract other medically relevant parameters such as heart rate (HR) and heart rate variability (HRV), respiration rate (RR), stroke volume (SV), cardiac output (CO), and information relating to thoracic fluids, e.g. thoracic fluid index (TFC) and general body fluids (FLUIDS). Certain physiological conditions can be identified from these parameters using one-time measurements; other conditions require observation of time-dependent trends in the parameters in order to identify the underlying condition. In all cases, it is important to measure the parameters with high repeatability and accuracy.

Some conditions require various physiological parameters to be measured over a relatively short period of time in order to identify the condition. For example, Holter monitors can characterize various types of cardiac arrhythmias by measuring HR, HRV, and ECG waveforms over periods ranging from a day to a few weeks. On the other hand, chronic diseases such as congestive heart failure (CHF) and end-stage renal disease (ESRD) typically require periodic measurements of FLUIDS and weight throughout the patient's life in order to identify the condition. Not surprisingly, patient compliance with measurement routines typically decreases as the measurement period increases. This is particularly true when measurements are made outside of a conventional medical facility, e.g., at the patient's home or in a residential facility such as a nursing home.

Furthermore, the measured values of some physiological parameters will vary with the location at which the parameters are measured, while those associated with other physiological parameters are relatively independent of the location at which the parameters are measured. For example, parameters such as HR, which depends on the time-dependent variation of R-R intervals associated with QRS complexes in ECG waveforms, are relatively insensitive to sensor positioning. Likewise, pulse oximetry (SpO2) and pulse rate (PR), as measured from photoplethysmogram (PPG) waveforms with a pulse oximeter, show little variance with measurement location.

On the other hand, measurements that depend on amplitude-dependent features in waveforms, such as TFC or FLUIDS, will be strongly dependent on the measurement location, e.g. the positioning of electrodes. In the case of TFC, for example, the measured value depends strongly on the sensed impedance between a set of electrodes. And this, in turn, will vary with the electrodes' placement. TFC deviation in the day-to-day placement of the electrodes can result in measurement errors. This, in turn, can lead to misinformation (particularly when trends of the measured parameters are to be extracted), thereby nullifying the value of such measurements and thus negatively impacting treatment.

Like TFC, measured values of blood pressure (BP), such as systolic (SYS), diastolic (DIA), and pulse (PP) pressures are typically sensitive to the location at which the parameter is measured. For example, blood pressure measured at the brachial artery with a sphygmomanometer (i.e. a manual blood pressure cuff) or with an oscillometric device (i.e. an automated blood pressure cuff measuring oscillometric waveforms) will typically be different from that measured at other locations on the body, such as the wrist, thigh, finger, or even the opposite arm. Mean arterial pressure (MAP) is less sensitive to position, as it is relatively constant throughout the body. Body (e.g. skin) temperature is similarly dependent on the location at which it is measured, although core temperature (TEMP), as measured from the ear or mouth, is relatively consistent from one location to another.

3. Sensors, Devices, and Relevant Physiology

Disposable electrodes that measure ECG and TBI waveforms are typically worn on the patient's chest or legs and include: i) a conductive hydrogel that contacts the patient's skin; ii) a Ag/AgCl-coated eyelet that contacts the hydrogel; iii) a conductive metal post that connects to a lead wire or cable extending from the sensing device; and iv) an adhesive backing that adheres the electrode to the patient. Unfortunately, during a measurement, the lead wires can pull on the electrodes if the device is moved relative to the patient's body, or if the patient ambulates and snags the lead wires on surrounding objects. Such pulling can be uncomfortable or even painful, particularly where the electrodes are attached to hirsute parts of the body, and this can inhibit patient compliance with long-term monitoring. Moreover, these actions can degrade or even completely eliminate adhesion of the electrodes to the patient's skin, and in some cases completely destroy the electrodes' ability to sense the physiological signals at various electrode locations.

Some devices that measure ECG and TBI waveforms are worn entirely on the patient's body. These devices have been developed to feature simple, patch-type systems that include both analog and digital electronics connected directly to underlying electrodes. Such devices, like the Holter monitors described above, are typically prescribed for relatively short periods of time, e.g. for a period of time ranging from a day to several weeks. They are typically wireless and include features such as Bluetooth® transceivers to transmit information over a short distance to a second device, which then transmits the information via a cellular radio to a web-based system.

SpO2 values are almost always measured at the patient's fingers, earlobes, or, in some cases, the forehead. In these cases, patients wear an optical sensor to measure PPG waveforms, which are then processed to yield SpO2 and PR values. TEMP is typically measured with a thermometer inserted into the patient's mouth, or with an optical sensor featuring an infrared-sensitive photodiode pointed into the patient's ear.

Assessing FLUIDS, TFC, weight, and hydration status is important in the diagnosis and management of many diseases. For example, ESRD occurs when a patient's kidneys are no longer able to work at a level needed for day-to-day life. The disease is most commonly caused by diabetes and high blood pressure, and is characterized by swings in SYS and DIA along with a gradual increase in FLUIDS throughout the body. Patients suffering from ESRD typically require hemodialysis or ultrafiltration to remove excess fluids. Thus, accurate measurement of this parameter and/or TFC to characterize ESRD can eliminate the need for empirical clinical estimations that often lead to over-removal or under-removal of fluids during dialysis, thereby preventing hemodynamic instability and hypotensive episodes (Anand et al., "*Monitoring Changes in Fluid Status With a Wireless Mul-*

*tisensor Monitor: Results From the Fluid Removal During Adherent Renal Monitoring (FARM) Study,"* Congest Heart Fail. 2012; 18:32-36). A similar situation exists with respect to CHF, which is a complicated disease typically monitored using a "constellation" of physiological factors, e.g., fluid status (e.g. FLUIDS, TFC), vital signs (i.e., HR, RR, TEMP, SYS, DIA, and SpO2), and hemodynamic parameters (e.g. CO, SV). Accurate measurement of these parameters can aid in managing patients, particularly in connection with dispensing diuretic medications, and thus reduce expensive hospital readmissions (Packer et al., *"Utility of Impedance Cardiography for the Identification of Short-Term Risk of Clinical Decompensation in Stable Patients With Chronic Heart Failure,"* J Am Coll Cardiol 2006; 47:2245-52).

CHF is a particular type of heart failure (HF), which is a chronic disease driven by complex pathophysiology. In general terms, HF occurs when SV and CO are insufficient to adequately perfuse the kidneys and lungs. Causes of this disease are well known and typically include coronary heart disease, diabetes, hypertension, obesity, smoking, and valvular heart disease. In systolic HF, ejection fraction (EF) can be diminished (<50%), whereas in diastolic HF this parameter is typically normal (>65%). The common signifying characteristic of both forms of heart failure is time-dependent elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Thus, early compensatory mechanisms for HF that can be detected fairly easily include increased RR and HR.

As CO is compromised, the kidneys respond with decreased filtration capability, thus driving retention of sodium and water and leading to an increase in intravascular volume. As the LVEDP rises, pulmonary venous congestion worsens. Body weight increases incrementally, and fluids may shift into the lower extremities. Medications for HF are designed to interrupt the kidneys' hormonal responses to diminished perfusion, and they also work to help excrete excess sodium and water from the body. However, an extremely delicate balance between these two biological treatment modalities needs to be maintained, since an increase in blood pressure (which relates to afterload) or fluid retention (which relates to preload), or a significant change in heart rate due to a tachyarrhythmia, can lead to decompensated HF. Unfortunately, this condition is often unresponsive to oral medications. In that situation, admission to a hospital is often necessary for intravenous diuretic therapy.

In medical centers, HF is typically detected using Doppler/ultrasound, which measures parameters such as SV, CO, and EF. In the home environment, on the other hand, gradual weight gain measured with a simple weight scale is likely the most common method used to identify CHF. However, by itself, this parameter is typically not sensitive enough to detect the early onset of CHF—a particularly important stage when the condition may be ameliorated simply and effectively by a change in medication or diet.

SV is the mathematical difference between left ventricular end-diastolic volume (EDV) and end-systolic volume (ESV), and represents the volume of blood ejected by the left ventricle with each heartbeat; a typical value is about 70-100 mL. CO is the average, time-dependent volume of blood ejected from the left ventricle into the aorta and, informally, indicates how efficiently a patient's heart pumps blood through their arterial tree; a typical value is about 5-7 L/min. CO is the product of HR and SV.

CHF patients—particular those suffering from systolic HF—may receive implanted devices such as pacemakers and/or cardioverter-defibrillators to increase EF and subsequent blood flow throughout the body. These devices may include circuitry and algorithms to measure the electrical impedance between different leads of the device. Some implanted devices process this impedance to calculate a "fluid index". As thoracic fluid increases in the CHF patient, the impedance typically is reduced, and the fluid index increases.

4. Clinical Solutions

Many of the above-mentioned parameters can be used as early markers or indicators that signal the onset of CHF. EF is typically low in patients suffering from this chronic disease, and it can be further diminished by factors such as a change in physiology, an increase in sodium in the patient's diet, or non-compliance with medications. This is manifested by a gradual decrease in SV, CO, and SYS that typically occurs between two and three weeks before hospitalization becomes necessary to treat the condition. As noted above, the reduction in SV and CO diminishes perfusion to the kidneys. These organs then respond with a reduction in their filtering capacity, thus causing the patient to retain sodium and water and leading to an increase in intravascular volume. This, in turn, leads to congestion, which is manifested to some extent by a build-up of fluids in the patient's thoracic cavity (e.g. TFC). Typically, a detectable increase in TFC occurs about 1-2 weeks before hospitalization becomes necessary. Body weight increases after this event (typically by between three and five pounds), thus causing fluids to shift into the lower extremities. At this point, the patient may experience an increase in both HR and RR to increase perfusion. Nausea, dyspnea, and weight gain typically grow more pronounced a few days before hospitalization becomes necessary. As noted above, a characteristic of decompensated HF is that it is often unresponsive to oral medications; thus, at this point, intravenous diuretic therapy in a hospital setting often becomes mandatory. A hospital stay for intravenous diuretic therapy typically lasts about 4 days (costing several thousands of dollars per day, or more), after which the patient is discharged and the above-described cycle may start over once again.

Such cyclical pathology and treatment is physically taxing on the patient, and economically taxing on society. In this regard, CHF and ESRD affect, respectively, about 5.3 million and 3 million Americans, resulting in annual healthcare costs estimated at $45 billion for CHF and $35 billion for ESRD. CHF patients account for approximately 43% of annual Medicare expenditures, which is more than the combined expenditures for all types of cancer. Somewhat disconcertingly, roughly $17 billion of this is attributed to hospital readmissions. CHF is also the leading cause of mortality for patients with ESRD, and this demographic costs Medicare nearly $90,000/patient annually. Thus, there understandably exists a profound financial incentive to keep patients suffering from these diseases out of the hospital. Starting in 2012, U.S. hospitals have been penalized for above-normal readmission rates. Currently, the penalty has a cap of 1% of payments, growing to over 3% in the next 3 years.

Of some promise, however, is the fact that CHF-related hospital readmissions can be reduced when clinicians have access to detailed information that allows them to remotely titrate medications, monitor diet, and promote exercise. In fact, Medicare has estimated that 75% of all patients with ESRD and/or CHF could potentially avoid hospital readmissions if treated by simple, effective programs.

Thus, in order to identify precursors to conditions such as CHF and ESRD, physicians can prescribe physiological monitoring regimens to patients living at home. Typically, such regimens require the use of multiple standard medical devices, e.g. blood pressure cuffs, weight scales, and pulse oximeters. In certain cases, patients use these devices daily and in a sequential manner, i.e. one device at a time. The patient then calls a central call center to relay their measured parameters to the call center. In more advanced systems, the devices are still used in a sequential manner, but they automatically connect through a short-range wireless link (e.g. a Bluetooth® system) to a "hub," which then forwards the information to a call center. Often, the hub features a simple user interface that presents basic questions to the patient, e.g. questions concerning their diet, how they are feeling, and whether or not medications were taken.

For such monitoring to be therapeutically effective, it is important for the patient to use their equipment consistently, both in terms of the duration and manner in which it is used. Less-than-satisfactory consistency with the use of any medical device (in terms of duration and/or methodology) may be particularly likely in an environment such as the patient's home or a nursing home, where direct supervision may be less than optimal.

SUMMARY OF THE INVENTION

In view of the foregoing, it would be beneficial to provide a monitoring system that is suitable for home use. Particularly valuable would be a system that is wireless and conveniently measures a collection of vital signs and hemodynamic parameters. Ideally, such a system would be easy to use, would improve measurement consistency, and feature a simple form factor that integrates into the patient's day-to-day activities. A monitoring system according to the invention, which facilitates monitoring a patient for HF, CHF, ESRD, cardiac arrhythmias, and other diseases, is designed to achieve this goal.

The inventive device described herein is a handheld device featuring an integrated form factor that fits in a patient's hand and measures all vital signs and some hemodynamic parameters from the human body. It transmits information it measures through a wireless interface to a web-based system, where it can be analyzed by a clinician to help diagnose a patient.

The inventive device and measurement methodologies are based in part on the discovery that the bio-impedance signals (e.g. TBI waveforms) used to determine vital signs and hemodynamic parameters can be measured over a conduction pathway that extends from the patient's wrist to a location on their thoracic cavity, e.g. their chest or belly button. (Additional conduction pathways we have discovered to be suitable include those that extend from the wrist to the torso, legs, opposing arm, or neck.) The form factor of the handheld device described herein accommodates such measurements with a system that is comfortable, easy to use, and includes re-usable electrodes to reduce costs. Measurements made by the handheld device suitably use the belly button as a 'fiducial' marker, as described in detail below. This location, which is present on nearly all patients, facilitates consistent, daily measurements that reduce errors due to positioning that normally impact impedance measurements. Other measurement locations, such as a nipple, mole or other birthmark, elbow, wrist joint, etc., may also be used as a fiducial marker. What is most important is that the patient positions the device consistently from one measurement to another. In this and other ways, the handheld device provides an effective tool for characterizing patients with chronic diseases, such as CHF, ESRD, and hypertension.

In one aspect, the invention provides a system for measuring bio-impedance waveforms (e.g. TBI waveforms) from a patient. The system features a rigid housing having a first portion configured to contact the patient's wrist and a second portion, integrated with the first portion and configured to be held against the patient's thoracic cavity. The rigid housing also encloses a circuit board. The first portion includes a first pair of electrodes and the second portion includes a second pair of electrodes, wherein one of the electrodes in each pair is configured to inject an electrical current into the patient's wrist or torso, and the other electrode in each pair is configured to measure a voltage associated with the injected electrical current. An electrical system disposed on the circuit board receives signals from the first and second pair of electrodes, and processes them to determine a time-dependent bio-impedance waveform. A processing system disposed on the circuit board processes the bio-impedance waveform to determine a physiological parameter.

In another aspect, the invention provides a method for monitoring a bio-impedance waveform from a patient. The method includes the following steps: 1) wearing or holding a handheld device configured, for example, as described above, with a first pair of electrodes contacting the wrist; 2) at the same time, contacting a region on the patient's thoracic cavity with another electrode-bearing portion of the handheld device, so that an electrode in the first pair of electrodes injects an electrical signal into the patient's wrist and an electrode in the second pair of electrodes injects an electrical signal into the patient's thoracic cavity; 3) measuring a time-dependent waveform by processing a voltage measured by an electrode in each of the first and second pairs of electrodes; and 4) processing the voltage to determine the bio-impedance waveform.

In another aspect, the invention provides a system for measuring vital signs and hemodynamic parameters from a patient. Here, the invention features a form factor generally similar to that described above, except that it includes a third portion for receiving one of the patient's fingers, preferably of the hand used to hold or wear the device. The first and second portions include pairs of electrodes, as described above. The third portion features an optical system having a light source and a photodetector. The overall system includes an electrical system that processes signals from the electrodes, as described above, to generate bio-impedance and electrocardiogram waveforms. The system also receives a signal from the photodetector and processes it to determine a photoplethysmogram waveform. A processing system disposed on a circuit board processes: 1) the bio-impedance waveform to determine an SV; 2) the electrocardiogram waveform to determine a HR; and 3) the photoplethysmogram waveform to determine an SpO2 value.

In another aspect, the invention provides a method for monitoring vital sign values from a patient. The method includes steps similar to those described above along with additional steps of: 1) inserting one of the patient's fingers into an opening having an optical system, which optical system comprises a light source and a photodetector; 2) processing a signal measured by the photodetector to determine a photoplethysmogram waveform; 3) additionally determining bio-impedance and electrocardiogram waveforms; 4) analyzing the bio-impedance waveform to determine SV; 5) analyzing the electrocardiogram waveform to determine HR; and 6) analyzing the photoplethysmogram waveform to determine an SpO2 value.

In yet another aspect, the invention provides a system for determining blood pressure using a handheld device as described above. In this aspect, the invention includes a handheld sensor that is generally similar to that described above. The handheld sensor also includes a processing system disposed on the circuit board and configured to: 1) process the bio-impedance waveform to determine a first fiducial point; 2) process the electrocardiogram waveform to determine a second fiducial point; 3) process the first and second fiducial points to determine a pulse transit time; and 4) process the inverse of the transit time and a pre-determined blood pressure calibration to determine the blood pressure value.

In exemplary embodiments, the blood pressure calibration includes values of SYS, DIA, and MAP. In other embodiments, the calibration includes a patient-specific relationship between a transit time and blood pressure. In still other embodiments, the blood pressure calibration includes both sets of parameters, e.g. initial blood pressure values and the patient-specific relationship between a transit time and blood pressure.

Typically, the handheld device includes a wireless transmitter for sending and receiving information to/from another wireless device, e.g., for use in connection with the blood pressure calibration. For example, the patient's weight may be sent to the device wirelessly from a digital scale. In preferred embodiments the transmitter is based on Bluetooth® or 802.11.

In another aspect, the invention features a handheld device, used to measure various biometric parameters, in which inflatable structures are covered with electrically conductive material. This allows the structures to sense pressure (including pressure oscillations) as well as to function as current-injecting or voltage-sensing electrodes.

In exemplary embodiments according to this aspect of the invention, the inflatable structures include a bladder that can be filled, e.g., with a fluid such as air, and the handheld device includes a pressure-delivery system including a pump. The pump connects to the bladder and, in embodiments, a valve, and it is configured to pump air into the bladder when the pump is activated. A pressure sensor connects to the bladder and is configured to measure a pressure within the bladder.

Suitably, the processing system features computer code that analyzes the set of pressure values to determine the blood pressure value. The computer code can run on, e.g., a microcontroller or microprocessor. For example, the pressure values can be a set of pressure-dependent oscillations that depend on the patient's blood pressure, and the computer code can analyze these to determine a blood pressure value. Typically, each pressure-dependent oscillation in the set of pressure-dependent oscillations is characterized by a pressure and amplitude value, and the computer code is further configured to determine the pressure-dependent oscillation having a maximum amplitude value. From this the system calculates the MAP. In related embodiments, the computer code is further configured to determine SYS from a first pressure-dependent oscillation characterized by an amplitude that, when divided by the maximum amplitude of the pressure-dependent oscillations, is substantially equivalent to a first pre-determined ratio (typically between 0.4-0.8, and most preferably about 0.6). In yet another related embodiment, the computer code is further configured to determine DIA from a second pressure-dependent oscillation characterized by an amplitude that, when divided by the maximum amplitude of the pressure-dependent oscillations, is substantially equivalent to a second pre-determined ratio (typically between 0.4-0.8, and most preferably about 0.7).

In embodiments, the set of pressure-dependent oscillations are measured while the pressure-delivery system inflates or deflates the flexible member.

The handheld device features an electrical impedance system having at least four electrodes, at least one of which is configured to inject an electrical current into the patient's body and at least one of which is configured to measure a signal induced by the injected electrical current and representative of biological impedance. A wireless system within the handheld device receives an SV calibration value. An internal processing system receives signals from the electrical impedance system and converts them into a set of impedance values, and analyzes the set of impedance values and the SV calibration to calculate SV.

In embodiments, the SV calibration includes a value representing the patient's weight, height, body composition, and/or age. These values are used to calculate a volume conductor, described in more detail below.

In embodiments, the processing system features computer code configured to analyze the set of impedance values to determine the stroke volume value. For example, the computer code can calculate a derivative of the set of impedance values to determine a $d\Delta Z(t)/dt$ waveform, from which it calculates a maximum value or an area of a pulse therein. The computer code can also analyze the $d\Delta Z(t)/dt$ waveform to determine an ejection time or a baseline impedance ($Z_0$) value. The computer code can then process these values to determine SV using Eq. 1:

$$SV \sim \frac{(d\Delta Z(t)/dt)_{max}}{Z_o} \times LVET \qquad (1)$$

or, alternatively, using Eq. 2:

$$SV \sim \sqrt{\frac{(d\Delta Z(t)/dt)_{max}}{Z_o}} \times LVET \qquad (2)$$

In embodiments, the handheld device (wirelessly) receives a weight value from a weight-measuring device, such as a scale. The processing system can then use the weight to determine SV from the equation:

$$SV = V_c \times \frac{(d\Delta Z(t)/dt)_{max}}{Z_o} \times LVET \qquad (3)$$

or, alternatively, using Eq. 4:

$$SV = V_c \times \sqrt{\frac{(d\Delta Z(t)/dt)_{max}}{Z_o}} \times LVET \qquad (4)$$

where $V_c$ is a volume conductor calculated from the value of weight and/or body composition.

In still other aspects, the system calculates CO by also measuring HR as described below (e.g. using an ECG waveform), and then collectively processing SV and HR (e.g., by taking the product) to determine CO.

In another aspect, the handheld device measures a PTT value from a patient, and then uses this and the blood pressure calibration to determine the patient's blood pressure value.

In embodiments, the processing system features computer code configured to: i) calculate a mathematical derivative of the impedance values to determine a set of derivative values; and ii) determine a local maximum of the set of derivative values to determine the first pulsatile component; and/or iii) determine a zero-point crossing of the set of derivative values to determine the first pulsatile component. The computer code may also be configured to: i) estimate the set of derivative values using a mathematical function; and ii) analyze the mathematical function to determine the first pulsatile component.

In embodiments, the computer code is configured to determine a local maximum of the cardiac rhythm values to determine the second pulsatile component, and the cardiac rhythm values are representative of an ECG waveform. For example, the computer code can be configured to determine a QRS complex (e.g. calculate the Q or, more likely, R point) in the ECG waveform to determine the second pulsatile component. It can also further process the cardiac rhythm values to determine a heart rate value, e.g. by calculating a time interval separating the first and second R points.

The measurement system described herein has many advantages. In particular, it features and easy-to-use device that a patient can use to measure all their vital signs, complex hemodynamic parameters, and basic wellness-related parameters. Such ease of use may increase compliance, thereby motivating patients to use it every day. And with daily use, the measurement system can calculate trends in a patient's physiological parameters, thereby allowing better detection of certain disease states and/or management of chronic conditions such as CHF, diabetes, hypertension, COPD, and kidney failure.

Still other advantages should be apparent from the following detailed description, and from the claims.

BRIEF DESCRIPTION OF THE DRAWINGS

FIG. 5A is an end view of the handheld device of FIG. 1 showing its inflatable electrodes inflated (to take a measurement);

FIG. 5B is an end view of the handheld device of FIG. 1 showing its inflatable electrodes deflated (before and after a measurement);

DETAILED DESCRIPTION

1. Product Overview

A handheld device according to the invention integrates measurement of all vital signs and some hemodynamic parameters from the human body into a single, easy-to-use device. More specifically, the device measures the following waveforms: 1) ECG; 2) pressure; 3) PPG; and 4) TBI. Digital electronics in the device process these waveforms to calculate the following numerical information: 1) SYS, DIA, and MAP; 2) SpO2; 3) HR and HRV; 4) RR; 5) TEMP; 6) SV; 7) CO; and 8) FLUIDS. It uses permanent, reusable components (e.g. electrodes), and transmits numerical and waveform information through a patient's mobile device to a web-based system.

The handheld device supplants more complex prior systems that include, e.g., multiple devices to measure vital signs and hemodynamic parameters. For example, such prior systems may include a separate blood pressure cuff, pulse oximeter, Holter monitor or patch-based system, and spirometer to measure vital signs. Determining hemodynamic parameters with prior systems is typically more complicated, and may require a bio-impedance and/or ultrasound machine to measure CO, SV, and FLUIDS.

Use of a single device, as opposed to multiple devices, can simplify operation and reduce the time required to measure the above-mentioned parameters. This, in turn, may increase the patient's compliance with a prescribed measurement regiment, as it is well established that daily use of devices that measure physiological parameters typically improves as the time and complexity involved with using such devices decreases. By consistently collecting physiological information on a daily basis, systems using the handheld device can calculate trends in the information. Such trends may indicate the progression of certain disease states in a manner that is improved relative to one-time measurements of certain parameters. For example, a value of FLUIDS corresponding to 15 Ohms, or an SV corresponding to 75 mL, has little value taken in isolation. But if these parameters decrease by 20% over a period of a few days, it can indicate that the patient's heart is pumping blood in a less efficient manner (as indicated by the SV), which in turn decreases perfusion of the patient's kidneys and causes them to retain more fluids (as indicated by the FLUIDS level). Trends such as these can indicate, for example, the onset of CHF. Similar, trends in BP can indicate a worsening in hypertension or hypotension. Indeed, most disease states are indicated by trends in one or, more commonly, multiple physiological parameters. The handheld device provides a simple solution for measuring these parameters and their trends.

Figure 1:
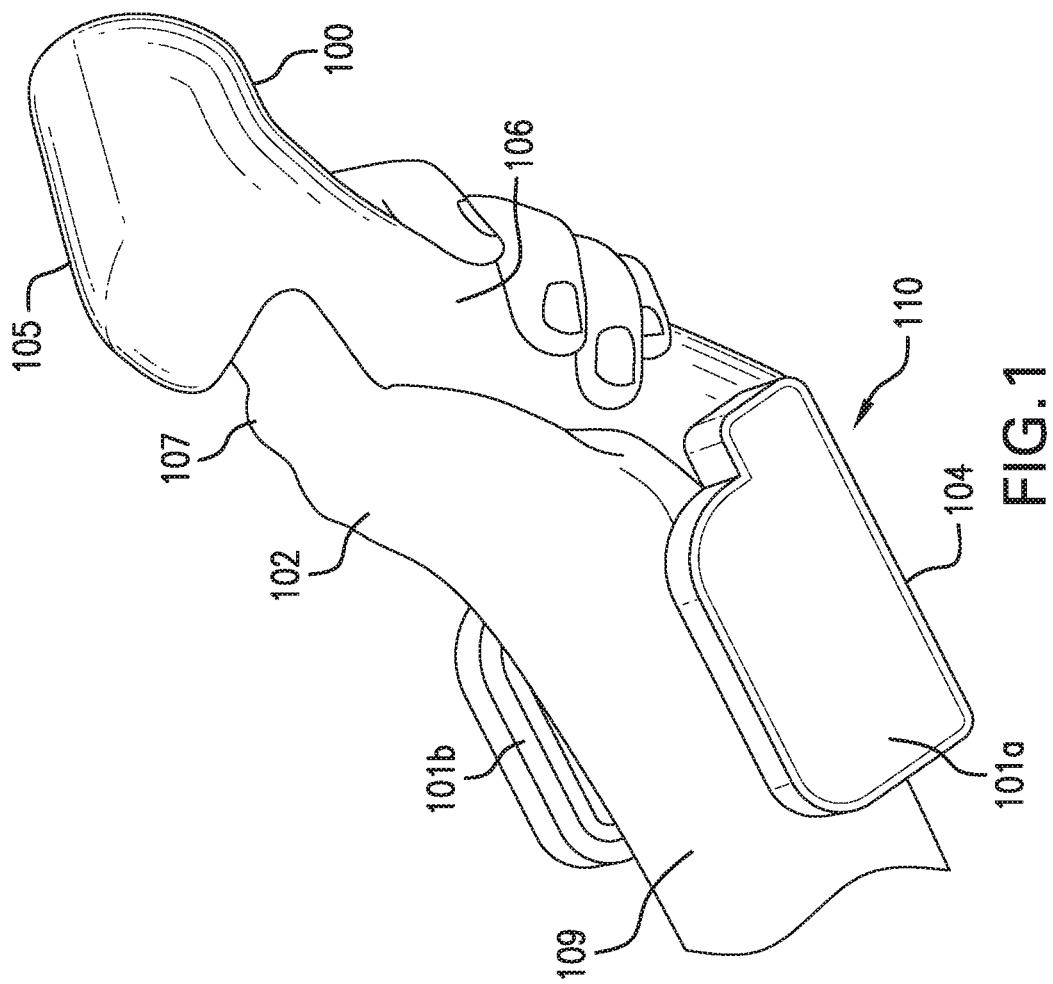
FIG. 1 is a perspective view of a handheld device according to the invention in use by a patient.

As shown in FIG. 1, a handheld device 100 according to the invention fits comfortably in a patient's left or right hand 102. The device 100 includes a generally C-shaped or U-shaped, wrist-receiving first portion 104 at its lower end with a space or opening configured to receive the patient's wrist. The space or opening is formed between a pair of generally parallel, spaced-apart walls or "wings" 101a, 101b, which extend from a base portion 101c of the wrist-receiving portion 104 and support an inflatable pressure-cuff system and a pair of cloth electrodes, not visible in FIG. 1 but described more fully below. Suitably, the cloth electrodes are coincident with the pressure-cuff system in that they are formed from conductive, stretchable fabric that overlies one or more inflatable bladders.

Figure 2A:
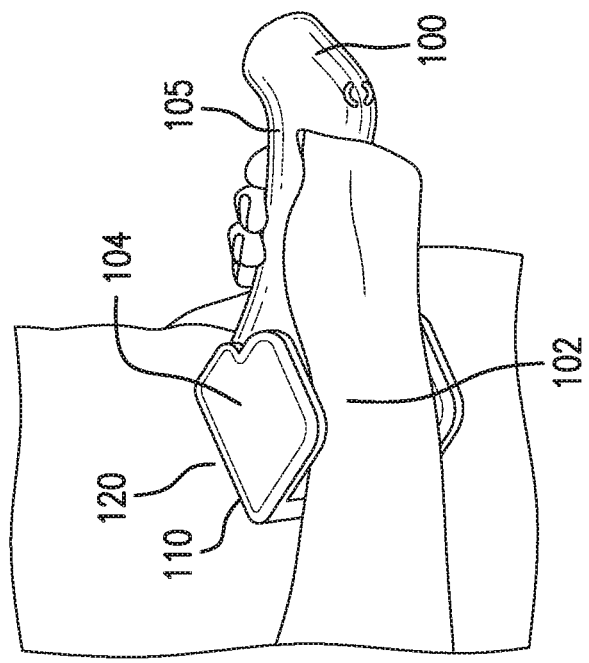
FIG. 2A is an illustration of the handheld device of FIG. 1 being pressed against a patient's belly button and used to measure vital signs and hemodynamic parameters according to inventive aspects of the invention.

A second, finger-receiving cavity portion 105 located at an opposite end of the device has an opening which is configured and positioned to receive the distal end of the patient's thumb when the device is held, as shown in FIGS. 1 and 2A. In alternate embodiments, the opening could be configured and positioned to receive the distal end of other digits of the patient's hand; however, positioning the opening along the lateral midline of the device so as to receive the user's thumb, and with the opening facing toward the wrist, makes it easier to grasp the device and insert one's thumb into the opening, as well as enabling the device 100 to be used with either hand. The cavity portion 105 houses an optical system—part of the pulse oximetry subsystem of the device 100—featuring light-emitting diodes (LEDs) that operate in the red (660 nm) and infrared (908 nm) spectral regions. A 'neck' 106 surrounds an internal circuit board and connects the C-shaped first portion 104 and the second, cavity portion 105. The neck 106 serves as a grip for the patient to hold the device, and may included additional electrodes, as described in more detail below. Mechanical and electrical components of these systems are explained in more detail with respect to FIG. 3.

To take a physiological measurement, as shown in FIG. 1, using their hand 102 the patient grasps the handheld device 100 by its neck 106; inserts their thumb 107 into the opening in the cavity portion 105; and inserts their wrist 109 into the opening or space in the C-shaped first portion 104. The patient gently wraps their fingers around the extended neck 106 so that the handheld device 100 is secure in their hand 102.

Figure 2B:
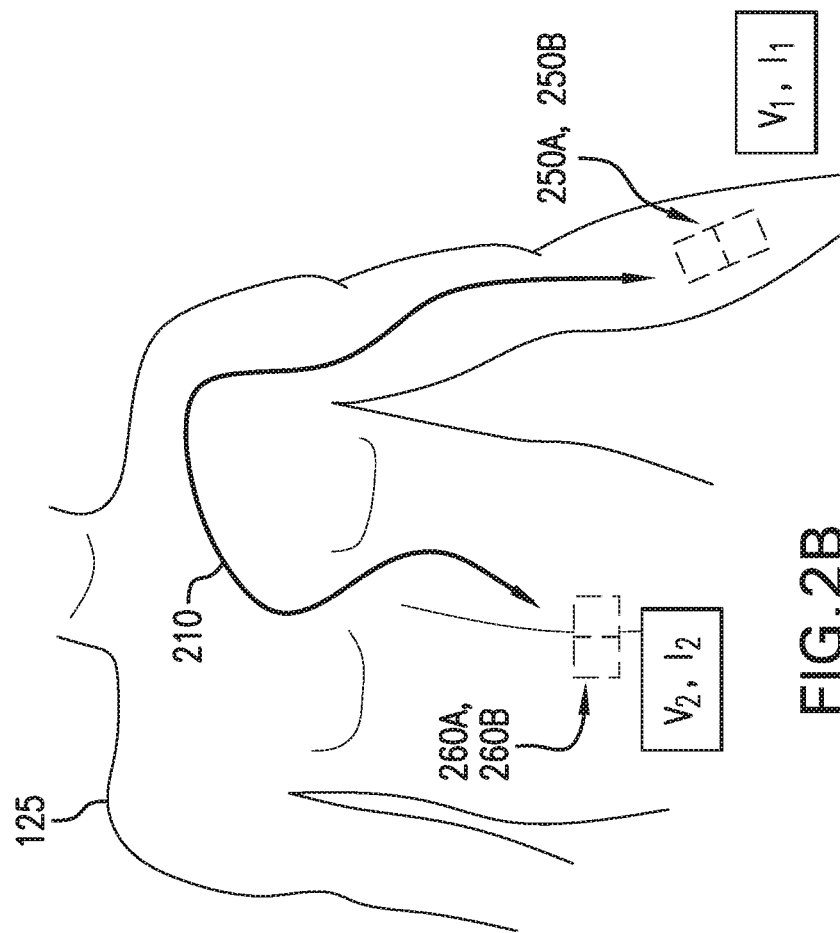
FIG. 2B is a schematic diagram of the conduction pathway created when the handheld device of FIG. 1 is pressed against a patient's belly button.

As shown in FIG. 2A, the patient simultaneously touches a bottom surface 110 of the handheld device 100 (e.g., an exposed, lower surface of base 101c) against bare skin near their belly button 120. The belly button serves as a good 'fiducial' marker that the patient can use daily as a measurement location. Alternatively, a permanent marker on the patient's body, e.g. their nipples, could also be used as a fiducial marker for taking measurement. The exposed bottom surface 110 of the handheld device 100 includes a pair of outwardly facing cloth electrodes (shown in more detail in FIGS. 3 and 4) that are similar to those included in the C-shaped first portion 104. As illustrated in FIG. 2B, with this configuration of the handheld sensor 100 and method of positioning the handheld sensor 100 against the body, two pairs of electrodes simultaneously and respectively contact locations 250A, 250B on the wrist (i.e., a distal portion of the patient's arm) and locations 260A, 260B on the belly of the patient 125. This establishes a relatively long conduction pathway 210, extending from the wrist, along the arm, and across the thoracic cavity and over which the handheld device 100 can measure ECG and TBI waveforms. More particularly, the conduction pathway 210, for example, extends from the radial and ulnar arteries in the patient's wrist, through the brachial artery, sub-clavian artery near the shoulder, and finally through the aorta (which is the largest artery in the body) and the heart. Depending on preferences, the exposed, outwardly facing electrodes could be positioned somewhere other than the bottom surface 110 of the sensor as a function of human anatomy and biomechanics, to facilitate bringing the exposed electrodes into contact with some other portion on the body beside the belly button or the nipple, e.g., the torso, the legs, the opposing arm, or the neck.

The handheld device described herein demonstrates that TBI waveforms measured with electrodes contacting the wrist have improved signal-to-noise ratios compared to waveforms measured with electrodes contacting the hands and/or fingers. Typically waveforms with relatively high signal-to-noise ratios yield more accurate measurements. For this reason, the handheld device described herein may be particularly effective in measuring parameters that are extracted from TBI waveforms, e.g. SV and CO. Without being bound by any theory, this may be because the wrist encloses blood-passing arteries (radial, ulnar) that are relatively large and uncomplicated compared to those in the hand. Thus such arteries are likely to yield TBI waveforms with relatively high signal-to-noise ratios.

The patient holds the handheld device 100 in this position for about 30 seconds, during which period of time the onboard microprocessor determines the various parameters of interest. When the measurement is complete an internal microprocessor controls a user-interface device (e.g., an LED or buzzer) to notify the patient. Once this occurs, an internal Bluetooth® transmitter in the handheld device 100 transmits numerical and waveform information to the patient's mobile device (not shown in the figure), which forwards it to a web-based system. There, a clinician, the patient, family member, etc. can review the information.

Figure 3:
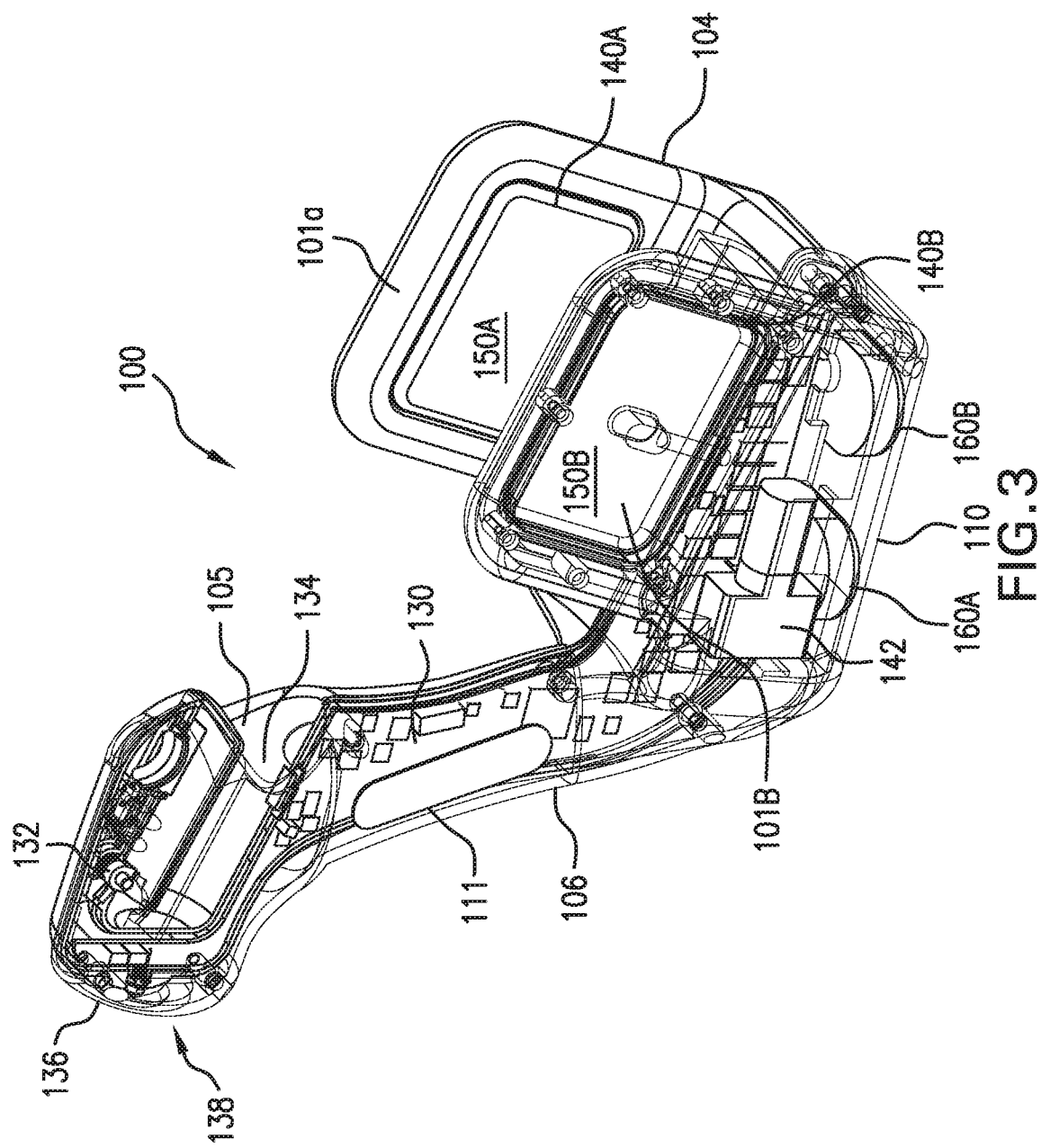
FIG. 3 is a schematic perspective view of the handheld device of FIG. 1, including some of its internal electronic systems.
Figure 4:
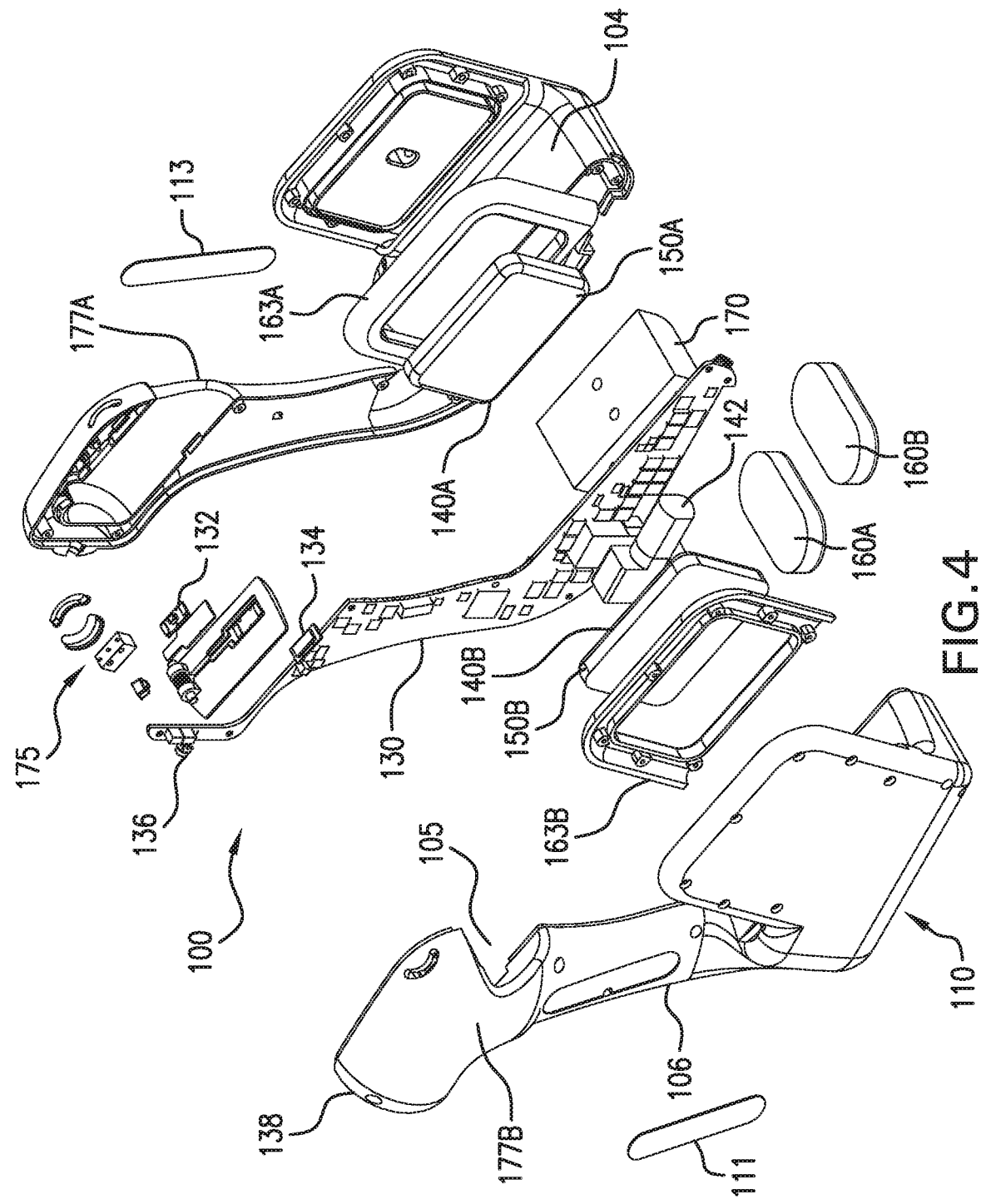
FIG. 4 is an exploded view of the handheld device of FIG. 3.

FIGS. 3 and 4 illustrate the handheld device's measurement electronics and internal components in more detail. In general, a housing of the handheld device 100 is constructed from two generally symmetric, right and left halves 177A, 177B, which are joined together along a longitudinal midline. The housing halves 177A, 177B are suitably formed (e.g., injection molded) from a rigid material, e.g., medical-grade plastic. A circuit board 130 is housed within an internal space formed by the right and left halves 177A, 177B of the handheld device's housing, primarily within the neck 106, and supports the electronics that drive each measurement. A battery pack 170, including two rechargeable lithium-ion batteries, powers the system. The batteries can be recharged through a standard USB connector (not shown in the figure) that connects through a cable to an AC/DC adaptor plugged into a wall outlet or, depending on power requirements, a USB port of a personal computer.

The handheld sensor 100 also includes an additional electrode 111 that is typically used as a drive electrode to reduce 60 Hz noise typically caused by common mode interference. This component is located on an outer portion of the neck 106 so as to make contact with the patient's skin (e.g. on their palms and/or fingers) when they grasp the neck 106. Typically, such an electrode and associated electrical circuitry is referred to as a 'right leg drive'. Right leg drive circuitry is known in the art, and is used to eliminate common-mode interference noise by actively canceling the interference. A second electrode 113, also located on an outer portion of the neck 106 so as to make contact with the patient's skin when they grasp the neck 106, may also be used to improve the performance of the handheld device's right leg drive circuitry.

The upper portion of the circuit board 130 extends to within the cavity portion 105 and includes a dual-emitting LED 132, which generates red and infrared optical wavelengths in the 660 nm and 908 nm region, and a photodetector (e.g., photodiode) 134. These components measure PPG waveforms using both red and infrared radiation, as is generally known in the art, but quite advantageously from one of the digits (e.g., the thumb) of the hand with which the patient holds the handheld sensor. This makes for a highly compact, easy-to-use, comprehensive device. A digital system within the circuit board processes the waveforms to determine SpO2. Generally speaking, such measurement is described in more detail in the following co-pending patent applications, the contents of which are incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013. In general and as explained in greater detail in these incorporated references, during an SpO2 measurement, the digital system alternately powers red and infrared LEDs within the dual-emitting LED 132. This process generates two distinct PPG waveforms. Using both digital and analog filters, the digital system extracts AC and DC components from the red (RED(AC) and RED(DC)) and infrared (IR(AC) and IR(DC)) PPG waveforms, which the digital system then processes to determine SpO2, as described in the above-referenced patent applications.

To measure TEMP, the handheld device 100 includes an infrared temperature sensor 136, which is mounted to an upper, forward-most portion of the circuit board 130. The infrared temperature sensor detects temperature "looking outwardly" from an upper, outer, forward-facing "nose" portion 138 of the cavity portion 105. More specifically, to measure TEMP, the handheld device 100 is held close to the patient's ear so that the outer portion 138 is adjacent to or pressed up against either the left or right ear. Because the temperature sensor is positioned where it is, the patient can take a temperature reading with the same device used to measure the other physiological parameters, and without even having to remove the device from his or her hand to do so. In this configuration, the infrared temperature sensor 136 detects infrared radiation (e.g. blackbody radiation) emitted from inside the ear, which it then converts to a temperature value using techniques known in the art. Suitably, the temperature sensor 136 is a fully digital system, meaning it receives the infrared radiation with an internal photodetector and, using an internal digital system, converts this to a temperature value that it sends through a serial interface (e.g. one based on a conventional UART or I2C interface) for follow-on processing.

A multi-color status LED assembly 175 indicates when the device turns on, a measurement is being taken, a measurement is complete, and data are being transmitted through Bluetooth. The multi-color status LED assembly 175 can change color and blink at different frequencies to indicate these states.

The C-shaped, wrist-receiving portion 104 is configured to measure physiological parameters using two complementary measurement modalities. According to one modality, the C-shaped portion measures BP, e.g. SYS, DIA, and MAP, by direct sensing of pressure. To that end, the wrist-receiving portion 104 includes a pair of inflatable/deflatable, elastomeric bladders 140A,B, which are mounted on or supported by the two generally parallel, spaced-apart walls or wings 101*a*, 101*b* that extend from the base 101*c* of the wrist-receiving portion 104; the walls form the space or opening in which the patient's wrist is received, as noted above and as illustrated in FIGS. 1 and 2A. (Other shapes of the bladder-supporting walls are also acceptable. For example, even a completely circular, wrist-surrounding ring-shaped structure through which the patient would insert their arm could be provided.) The bladders 140A,B are configured and arranged to inflate inwardly, i.e., into the wrist-receiving space or opening, as illustrated in FIGS. 5A and 5B. A pair of plastic supports 163A, 163B hold the inflatable bladders 140A,B in place on their respective walls. Additionally, the plastic supports 163A, 163 B clamp down on stretchable cloth electrodes 150A,B, addressed below, which overlie the bladders.

A small pneumatic pump system 142, controlled by the digital system on the circuit board 130, inflates the bladders 140A,B to measure BP. In general, such pump systems are known in the art for use in connection with blood-pressure monitors such as those typically sold for home use. The pump system 142 includes a diaphragm pump; a solenoid-controlled valve to maintain or release pressure within the bladders; and suitable airline tubing leading into the bladders.

Gradual inflation of the bladders 140A,B slowly compresses the patient's radial artery. As it compresses, heartbeat-induced blood-flow within the artery generates slight pressure pulsations. These create a small pressure increase in the bladders that are detected by a pressure-measuring system (not shown in the figure) within the circuit board 130, as known in the art. This yields a pressure waveform that features amplitudes of the pressure pulsations plotted against the pressure applied by the inflatable bladders 140A, B. The pressure waveform typically features a bell-shaped curve when the amplitude of each pressure pulsation is plotted against the pressure applied. The digital system processes the bell-shaped curve to determine blood pressure according to the well-known technique of oscillometry. Such a technique is described in detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013. To summarize, MAP corresponds to the applied pressure that yields the maximum amplitude of the bell-shaped curve. SYS and DIA are determined, respectively, from applied pressures that yield well-defined amplitudes on the high-pressure and low-pressure sides of MAP. More specifically, SYS typically corresponds to the applied pressure that yields a pulse amplitude on the high-pressure side of MAP that, when divided by the pulse amplitude corresponding to MAP, has a ratio of about 0.4. DIA typically corresponds to the applied pressure that yields a pulse amplitude on the low-pressure side of MAP that, when divided by the pulse amplitude corresponding to MAP, has a ratio of 0.6. Other ratios can also be used to calculate SYS and DIA according to oscillometry.

During inflation, patches of conductive fabric disposed on the outer, wrist-contacting surface of the bladders 140A,B detect bio-electric signals. These are processed by analog circuitry associated on the circuit board 130 to generate ECG and TBI waveforms, as described in more detail below.

The handheld device 100 can also measure blood pressure according to an alternative direct-pressure-based technique. This technique involves monitoring PPG waveforms generated by the SpO2 measuring system (i.e., by either red or infrared wavelengths emitted by the dual-emitting LED 132 and detected by the photodetector 134) while the inflatable bladders 140A,B apply pressure to the patient's radial artery. Here, the applied pressure slowly reduces blood flow through the artery, causing heartbeat-induced PPG-waveform pulsations (i.e. pulsations in the RED(AC) or IR(AC) components of the PPG waveforms) to slowly increase, and then gradually decrease. As with oscillometry, the maximum amplitude of the pulsations typically corresponds to an applied pressure equal to MAP. The pulsations are completely eliminated when the applied pressure is equal to SYS, since at this pressure the radial artery is fully occluded, thus ceasing all blood flow. DIA can be determined from MAP and SYS using equations described in the above-referenced patent applications, the contents of which have been previously incorporated herein by reference.

The other modality by which the C-shaped, wrist-receiving portion 104 measures physiological parameters is by processing bioelectric signals. In particular, the two pairs of cloth electrodes are provided to measure bioelectric signals, which then pass to the associated analog circuitry provided on the circuit board 130. The analog circuitry processes the signals to generate ECG and TBI waveforms, which the analog-to-digital converter and microprocessor then, respectively, digitize and process to determine HR and HRV, RR, SV, CO, and TFC. As indicated above, one pair of electrodes is located within the C-shaped wrist-receiving portion 104, and these electrodes are arranged to contact the patient's wrist when it is received within the space or opening of that portion. The other pair of cloth electrodes 160A, 160B is located along the bottom surface 110 of the wrist-receiving portion 104. During use the electrodes 160A, 160B contact a second portion of the patient (e.g. belly button) to establish the conduction pathway 210 as described above.

Believed to be unique to the handheld sensor 100, the wrist-contacting electrodes 150A, 150B are coincident with (i.e., overlie) the inflatable bladders 140A, 140B, respectively, such that the overall system includes what are effectively inflatable electrodes. As a result, when the bladders are inflated in connection with measuring BP via direct, mechanical measurement of pressure, the electrodes are pressed firmly against the patient's skin, thereby enhancing electrical contact and accuracy/reliability of the electrophysiological measurements being taken. Additionally, such an arrangement facilitates the compact, self-contained form factor of the handheld sensor 100.

To this end, and as shown in more detail in FIGS. 5A and 5B, the electrodes 150A, 150B are formed from a stretchable, conductive fabric that is stretched over the inflatable bladders. In general, the electrode material is conductive fabric that has conductive elements interwoven in an elastic material. Resistivity is essentially 0 Ohms in both stretched and unstretched configurations. Suitably, the fabric is able to stretch by at least 25% along at least one dimension when the inflatable bladder is inflated, and preferably it is able to stretch by roughly 50% of its original dimension when force is applied to it. Although it is not required, the torso-contacting or belly-contacting electrodes 160A, 160B may also be formed from the same stretchable material. In this way all the electrodes 150A, 150B, 160A, 160B) have a similar skin/electrode impedance, which can be advantageous for ECG and TBI measurements.

As described above, the electrodes 150A,B and 160A,B are used to measure time-dependent ECG and TBI waveforms, and the digital system within the circuit board 130, in turn, processes the ECG and TBI waveforms to determine the above-enumerated values (HR and HRV, RR, SV, CO, and TFC). During a measurement, one electrode (e.g., 150B) in the C-shaped wrist-receiving portion 104 and one electrode (e.g., 160B) on the bottom surface 110 measure signals that the digital system processes using differential amplification to determine an ECG waveform. This waveform features heartbeat-induced pulses that, informally, mark the beginning of the cardiac cycle. Typically, the pulses include a sharp feature, called a QRS complex, which indicates electrical activity in the heart. The time separating neighboring QRS complexes is inversely related to the patient's HR. Typically, HR is calculated from a collection of QRS complexes spanning a short period of time, e.g. 30 seconds. The variation in heart rate determined during this period is the HRV, which is known to relate to cardiac function.

The handheld device's bio-impedance measurement system "shares" electrodes with the ECG measurement system. For bio-impedance, one electrode (e.g., 150A) in the C-shaped wrist-receiving portion 104 and one electrode (e.g., 160A) on the bottom surface 110 of the device inject a high-frequency (e.g., 100 kHz), low-amplitude (e.g., 6 mA) current into the patient's body. The current injected by the two electrodes 150A, 160A is out of phase by 180.degree. The other two electrodes (e.g., 150B, 160B) measure a voltage that, with follow-on processing, indicates the resistance (or impedance) encountered by the injected current. The voltage relates to the resistance (or impedance) through Ohms Law. Typically, a bio-impedance circuit within the circuit board measures TBI waveforms, which are separated into an AC waveform that features relatively high-frequency features (typically called $\Delta Z(t)$), and a DC waveform that features relatively low-frequency features (typically called $Z_0$). This technique for measuring $\Delta Z(t)$ and $Z_0$, called bio-impedance, is described in detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013.

Physiological processes within the body modulate $\Delta Z(t)$ and $Z_0$ waveforms generated by the handheld device's bio-impedance measurement system. Thus processing these waveforms can yield parameters that correspond to the physiological processes. As shown in FIG. 2B, when used as described above on a patient 125, the handheld device injects current (indicated by I1, I2) and detects voltage (indicated by V1, V2) over a conduction pathway 210 that extends from locations 250A, 250B near the patient's wrist to locations 260A, 260B near their belly button. The conduction pathway 210 passes through the patient's thoracic cavity, which contains vital organs such as the heart and lungs. Physiological processes that take place within the thoracic cavity modulate the TBI waveform. For example, respiratory effort (i.e. breathing) changes the capacitance of the chest, thus imparting a series of low-frequency undulations (typically 5-30 undulations/minute) on the $\Delta Z(t)$ waveform. The handheld device's digital system processes these oscillations to determine RR.

Blood is a decent electrical conductor, and thus blood pumped by the heart's left ventricle into the aorta modulates impedance in the thoracic cavity 220 (as well as other regions spanned by the conduction pathway 201, e.g. the brachial artery located in the patient's bicep). These modulations manifest as heartbeat-induced cardiac pulses on the $\Delta Z(t)$ waveform. They can be processed to determine SV as described in detail in the following co-pending patent applications, the contents of which have been previously incorporated by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013. The handheld device determines CO, which is the product of SV and HR, using a simple calculation.

Fluids (e.g. TFC) also conduct the injected current. Thus, fluids that accumulate in the thoracic cavity 220 affect the impedance within the conduction pathway 201 in a low-frequency (i.e. slowly changing) manner, and can be detected by processing the $Z_0$ waveform. Typically, the $Z_0$ waveform features an average value of between about 10-30 Ohms, with 10 Ohms indicating relatively low impedance and thus high fluid content (e.g. the patient is 'wet'), and 30 Ohms indicating a relatively high impedance and thus low fluid content (e.g. the patient is 'dry'). Time-dependent changes in the average value of $Z_0$ can indicate that the patient's fluid level is either increasing or decreasing. An increase in fluid level, for example, may indicate the onset of CHF.

2. Other Measurements—Bioreactance

Other measurement systems can be incorporated into the handheld device 100. For example, the cloth electrodes 150A,B, 160A,B described above, coupled with an additional circuit that measures a phase change in the injected current, can also be used to perform a measurement called bio-reactance. During a bio-reactance measurement, the phase difference between the injected currents and the detected currents is measured by the bio-reactance circuit and ultimately processed with the digital system on the circuit board to generate a bio-reactance waveform. The difference in phase in the bio-reactance waveform is due to the current being slowed down by the capacitive properties of cell membranes within the conduction pathway 210. The baseline phase difference, $\Phi a$, is estimated from the DC component of the bio-reactance waveform. $\Phi a$ is used to calculate tissue composition, described in more detail below. The AC component of the waveform can be used to track respiration and cardiac function as described above.

Bio-reactance, when combined with bio-impedance, can be used to measure physiological parameters related to body composition (e.g. fat, muscle, and fluid in the patient's body) and the progression of disease states. More specifically, bio-impedance and bio-reactance measurements analyze the resistance and reactance of the user's tissue—along with biometric parameters such as height, weight and age—to generate accurate estimates of the composition of the tissue in the abdomen, chest, and arm. Height, weight, and age, for example, can be input to the GUI of the patient's mobile device, and wirelessly transmitted to the handheld device for follow-on analysis.

$\Phi a$ and $Z_0$ are then used to calculate the resistance ($Z_0 \cos(\Phi a)$) and the reactance ($Z_0 \sin(\Phi a)$) of the tissue in the abdomen, chest, and right arm. Resistance and reactance have been shown to be predictive of tissue composition. For example, fatty tissue is far more conductive than fat-free tissue. Therefore, a tissue's resistance is largely governed by the mass of the fat-free tissue present. This makes the inverse of a tissue's resistance a good estimator of that tissue's fat-free mass. Similarly, cell membranes have capacitive properties that cause phase changes in current that passes through the body. The greater the concentration of cells in the tissue, the greater the change in phase. When coupled with resistance, reactance can thus distinguish changes in fat from changes in fluid due to the differences in the cellularity of fat and extracellular fluid. Specifically, it has been shown that resistance and reactance—coupled with height, weight and age—can predict fat-free mass and body-fat mass as accurately as the "gold-standard" method—air displacement plethysmography. This is described in the following journal article, the contents of which are incorporated herein by reference: *Body fat measurement by bioelectrical impedance and air displacement plethysmography: a cross-validation study to design bioelectrical impedance equations in Mexican adults*; Nutrition Journal; 6: (2007). When fat-free mass, body-fat mass, and weight are measured, the root cause of changes in weight can be identified. Changes in fluid retention can signal the onset or reoccurrence of numerous medical conditions, such as CHF and ESRD. By measuring both reactance and resistance, the handheld device can distinguish changes in fluid retention from changes in tissue mass. This enables reliable tracking of this important parameter at home, on a daily basis.

3. Other Measurements—Pulse Transit Time

Figure 6:
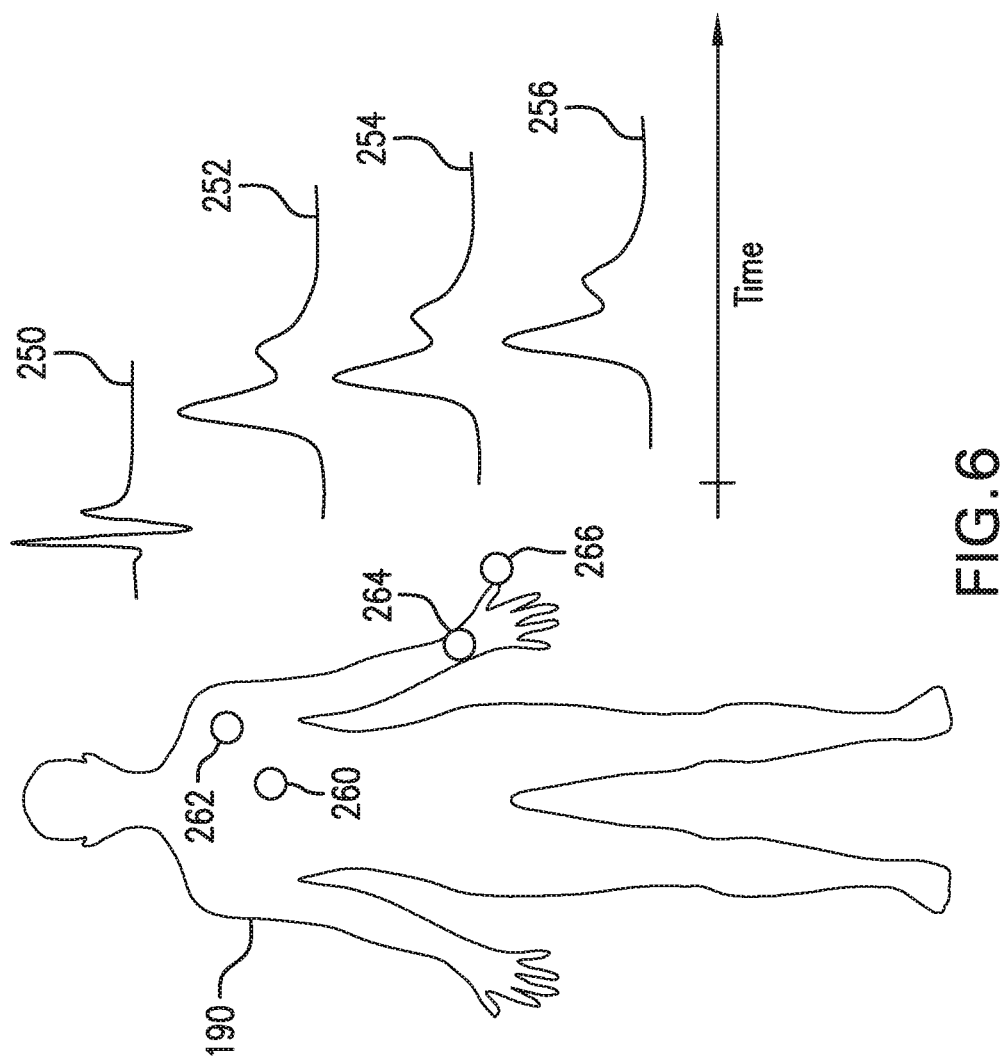
FIG. 6 is a schematic drawing showing locations on the human body were the handheld device can be used to measure physiological waveforms having pulsatile components.

As shown in FIG. 6, the handheld device measures from a patient 190 heartbeat-induced pulsatile components from the following waveforms: ECG 250, TBI 252, pressure 254, and PPG 256. As indicated in the figure, the handheld device samples pulsatile components in these waveforms along different portions of the patient's body, with each portion separated from the source of the pulsatile components—the patient's heart—by a sequentially increasing distance. For example, optics (LED 132, photodetector 134) within the finger-receiving cavity portion 105 of the handheld device measure pulsatile components in the PPG waveform 256, sampled from arteries within the patient's thumb 266. The inflatable bladders in the C-shaped wrist-receiving portion 104, coupled with pressure-measuring electronics, sense pulsatile components from the pressure waveform 254 measured from the patient's wrist 264. Cloth electrodes and the bio-impedance (and optionally bio-reactance) circuits measure pulsatile components in the $\Delta Z(t)$ waveform 252, which primarily senses blood flow from the heart's left ventricle into the aorta 262. And the QRS complex of the ECG waveform 250 is a pulsatile component that indicates initial electrical activity in the patient's heart 260 and, informally, marks the beginning of the cardiac cycle.

Thus detection and analysis of each of the above-described pulsatile components indicates blood flow through the patient's body. More specifically, the digital system in the handheld component can analyze the pulsatile components to determine parameters such as pulse arrival time (PAT), pulse transit time (PTT), and vascular transit time (VTT). Such transit times can be used, for example, to calculate blood pressure, e.g. SYS, DIA, and MAP. This methodology is described in more detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013.

Figure 7:
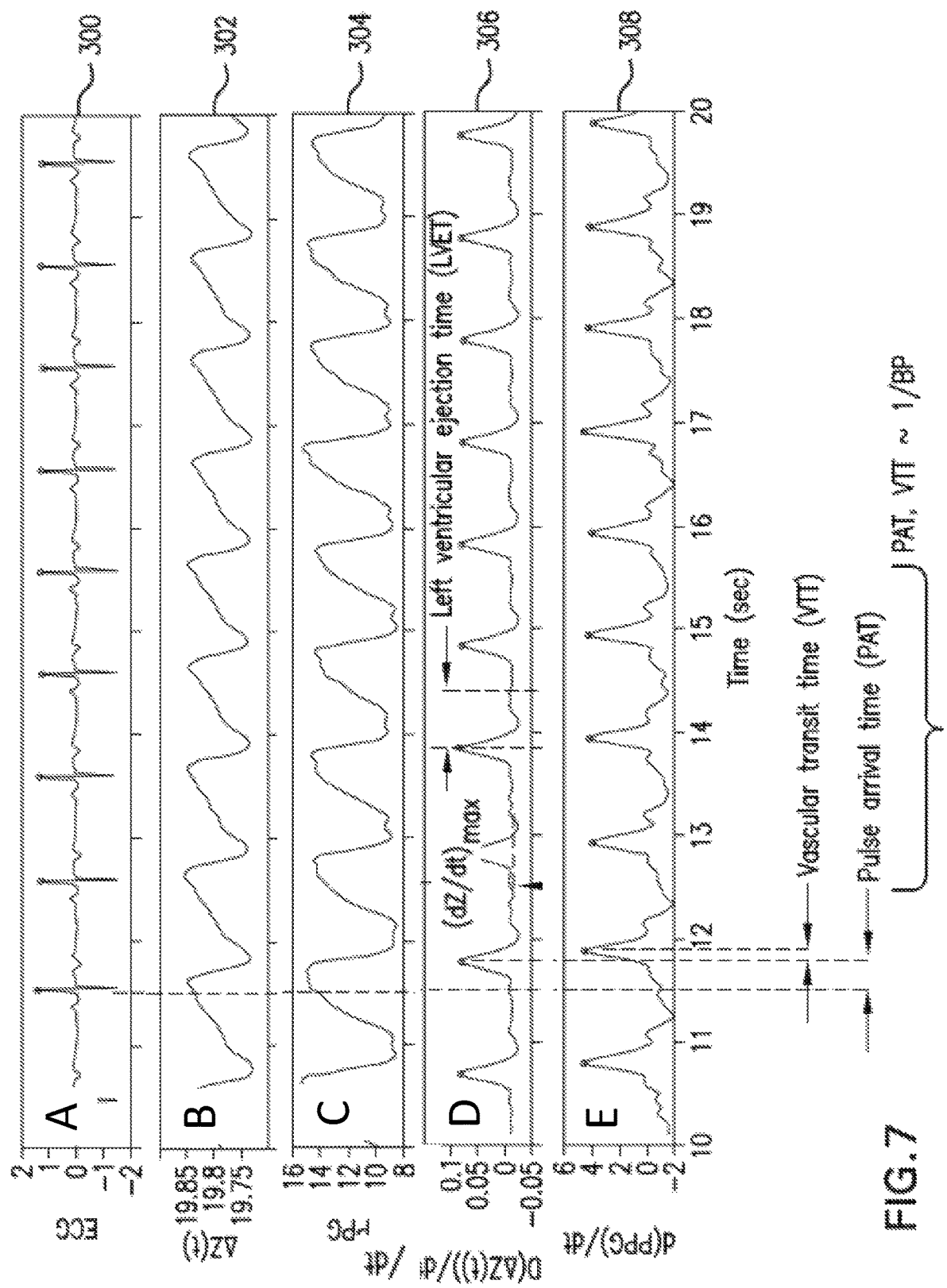
FIG. 7 is a plot of time-dependent ECG, $\Delta Z(t)$, PPG, $d(\Delta Z(t))/dt$, and $d(PPG)/dt$ waveforms measured with the handheld device shown in FIG. 1.

To summarize, FIG. 7 shows the following time-dependent waveforms, as measured by the handheld device: ECG (plot 300, labeled 'A'), $\Delta Z(t)$ (plot 302, labeled 'B'), PPG (plot 304, labeled 'C'), $d(\Delta Z(t))/dt$ (plot 306, labeled 'D'), and d(PPG)/dt (plot 308, labeled 'E'). As shown in plots 300 and 302, individual heartbeats produce time-dependent pulses in both the ECG and ΔZ(t) waveforms. As is clear from the data, pulses in the ECG waveform precede those in the ΔZ(t) waveform. The ECG pulses—each featuring a sharp, rapidly rising QRS complex—mark the beginning of the cardiac cycle.

ΔZ(t) pulses follow the QRS complex by about 100 ms and indicate blood flow through arteries in the region of the body where the cloth electrodes make contact with the skin. During a heartbeat, blood flows from the patient's left ventricle into the aorta; the volume of blood that leaves the ventricle is the SV. Blood flow periodically enlarges this vessel, which is typically very flexible, and also temporarily aligns blood cells (called erythrocytes) from their normally random orientation. Both the temporary enlargement of the vessel and alignment of the erythrocytes improves blood-based electrical conduction, thus decreasing the electrical impedance as measured with ΔZ(t). The d(ΔZ(t))/dt waveform (plot 306) shown in FIG. 7 is a first mathematical derivative of the raw ΔZ(t) waveform, meaning its peak represents the point of maximum impedance change.

A variety of time-dependent parameters can be extracted from the ECG and TBI waveforms. For example, as noted above, it is well know that HR can be determined from the time separating neighboring ECG QRS complexes. Likewise, left ventricular ejection time (LVET) can be measured directly from the derivative of pulses within the ΔZ(t) waveform, and is determined from the onset of the derivatized pulse to the first positive-going zero crossing. Also measured from the derivatized pulses in the ΔZ(t) waveform is $(d\Delta Z(t)/dt)_{max}$, which is a parameter used to calculate SV as described above.

The time difference between the ECG QRS complex and the peak of the derivatized ΔZ(t) waveform represents a pulse arrival time PAT, as indicated in FIG. 7. This value can be calculated from other fiducial points, including, in particular, locations on the ΔZ(t) waveform such as the base, midway point, or maximum of the heartbeat-induced pulse. Typically, the maximum of the derivatized waveform is used to calculate PAT, as it is relatively easy to develop a software beat-picking algorithm that finds this fiducial point.

PAT correlates inversely to SYS, DIA, and MAP, which can be calculated as described in the above-referenced patent applications using patient-specific slopes for SYS and DIA, measured during a calibration measurement. (Such a measurement can, for example, be performed with the inflatable bladders and optical systems described above.) Without the calibration, PAT only indicates relative changes in SYS, DIA, and MAP. The calibration yields both the patient's immediate values of these parameters. Multiple values of PAT and blood pressure can be collected and analyzed to determine patient-specific slopes, which relate changes in PAT with changes in SYS, DIA, and MAP. The patient-specific slopes can also be determined using predetermined values from a clinical study, and then combining these measurements with biometric parameters (e.g. age, gender, height, weight) collected during the clinical study.

In embodiments of the handheld device, waveforms like those shown in FIG. 7 can be processed to determine PAT. The handheld device can use this parameter, combined with a calibration determined as described above, to determine blood pressure without a physical-pressure-applying mechanism. Typically PAT and SYS correlate better than PAT and DIA.

Pulse pressure (PP) can be used to calculate DIA from SYS, and can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET) to each other. The slope can be estimated from a universal model that, in turn, is determined using a population study.

Alternatively, a slope tailored to the individual patient can be used. Such a slope can be selected, for example, using biometric parameters characterizing the patient as described above.

Here, PP/SV slopes corresponding to such biometric parameters are determined from a large population study and then stored in computer memory on the handheld device. When a device is assigned to a patient, their biometric data is entered into the system, e.g. using a GUI operating on a mobile device, that transmits the data to the handheld device via Bluetooth®. Then, an algorithm processes the data and selects a patient-specific slope. Calculation of PP from SV is explained in the following reference, the contents of which are incorporated herein by reference: "*Pressure-Flow Studies in Man. An Evaluation of the Duration of the Phases of Systole,*" Harley et al., *Journal of Clinical Investigation*, Vol. 48, p. 895-905, 1969. As explained in this reference, the relationship between PP and SV for a given patient typically has a correlation coefficient r that is greater than 0.9, which indicates excellent agreement between these two properties. Similarly, in the above-mentioned reference, SV is shown to correlate with the product of PP and LVET, with most patients showing an r value of greater than 0.93 and the pooled correlation value (i.e., the correlation value for all subjects) being 0.77. This last value indicates that a single linear relationship between PP, SV, and LVET may hold for all patients.

More preferably, PP is determined from SV using relative changes in these values. Typically, the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: "*Pulse pressure variation and stroke volume variation during increased intra-abdominal pressure: an experimental study,*" Didier et al., *Critical Care*, Vol. 15:R33, p. 1-9, 2011. Here, the relationship between PP variation and SV variation for 67 subjects displayed a linear correlation of r=0.93, which is an extremely high value for pooled results that indicates a single, linear relationship may hold for all patients.

From such a relationship, PP can be determined from the impedance-based SV measurement, and SYS can be determined from PAT. DIA can then be calculated from SYS and PP.

Another parameter, VTT, can be determined from pulsatile components in the ΔZ(t) (or d(ΔZ(t))/dt) waveform and the PPG (or d(PPG)/dt) waveform. FIG. 7 shows in more detail how VTT is determined. It can be used in place of PAT to determine blood pressure, as described above. Using VTT instead of PAT in this capacity offers certain advantages, namely, lack of signal artifacts such as pre-injection period (PEP) and isovolumic contraction time (ICT), which contribute components to the PAT value but which are not necessarily sensitive to or indicative of blood pressure.

Figure 8:
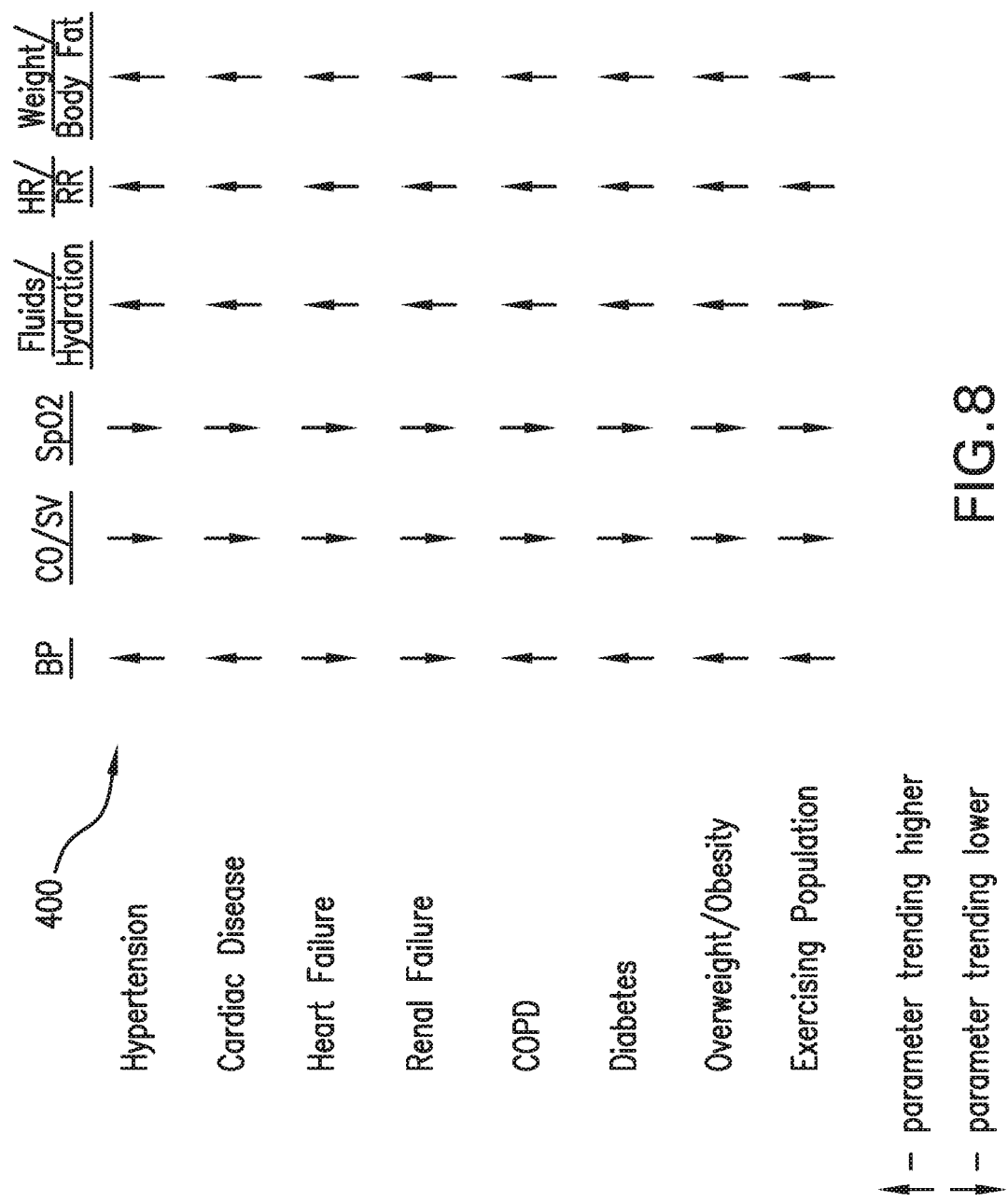
FIG. 8 is a table showing various physiological conditions and how they can be predicted by trends in certain physiological parameters.

In general, the overarching purpose of a handheld device according to the invention, as described above, is to make daily measurements of a wide range of physiological parameters that, in turn, can be analyzed to diagnose specific disease states. As described above, it is often the time-dependent trends in the physiological parameters that provide the best indication of such disease states. In general, it is a collection of trends in multiple physiological parameters that often serve as the best marker for the onset of disease states. In this regard, FIG. 8 shows, for example, a table 400 indicating how trends in different physiological parameters can be used to diagnose disease states such as hypertension, cardiac disease, heart failure (including CHF), renal failure (including ESRD), chronic obstructive pulmonary disease (COPD), diabetes, and obesity. In addition, the table 400 indicates how such trends may show beneficial progress to a population actively involved in exercise.

4. Other Embodiments

Other embodiments are within the scope of the invention. For example, measurement electronics used within the handheld device can be packaged in form factors that differ from those described above. Such form factors should make measurements along a suitably long conduction pathway. This pathway can also be different than that described above. For example, it may begin in the chest (as opposed to the belly button) or shoulder, and terminate in the fingers (as opposed to the wrist).

The handheld device can also be coupled to other systems that measure other parameters from a patient. Here, 'coupled' typically means information passes between the handheld device and the other systems through a wired or, more preferably, wireless interface. For example, the device can be coupled to a weight-measuring device through a Bluetooth™ or WiFi™ interface. The weight-measuring device can be a standard weight scale, or a 'digital floormat' as described in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013.

In other embodiments, the device may include a flexible or bendable neck, e.g., to accommodate various dimensions and/or geometries of the fingers relative to the hand. In such embodiments, the joint connecting the finger-receiving, oximetry-sensor portion of the device and the wrist-receiving, inflatable-bladder portion of the device would house a flex circuit connecting the circuitry in the neck to that in the base of the device. The joint can be composed of an elastic material (e.g. rubber) such that the neck can be extended further and moved closer to the bladder. Similarly, in still further embodiments, the walls or "wings" on which the inflatable bladders are supported could be joined to the base or bottom of the wrist-receiving portion of the device by more flexible joints. Since there is no circuitry within the walls or wings, no flex circuit would be required; instead a simple elastic material (e.g., a solid rubber boot) would allow the wings to flex and bend outwards in order to accommodate patients of varying wrist size.

In further embodiments, the device may have a hinged oximetry sensor. The sensor would have a hinge near the tip of the thumb such that it clamps down on the patient's thumb (like a spring-loaded clothespin) and applies a constant pressure to this appendage. This would ensure that the sensor accommodates patients of varying thumb size, and may also improve the signal-to-noise ratio of the PPG waveform it measures.

In further embodiments, the device may include a cuff-like mechanism that completely encircles the patient's wrist, instead of the wings or arms that only partially encircle it. The cuff could be composed of an elastic material (e.g. rubber) or an inelastic material (e.g. nylon) that wraps around the patient's wrist, with a fastening mechanism at the top (e.g. Velcro, magnet). The circuitry would still be located in the base of the cuff, and a rigid material (e.g. plastic) would house it for protection. In other embodiments, the device may be entirely constructed of a flexible material (e.g. rubber), with rigid components only housing the main circuitry and flex circuits linking the circuit in the cuff to the circuit in the oximetry sensor. In other embodiments, the device may take on more of a fingerless-glove-like form, covering the entire hand, wrist and thumb of the patient. This embodiment would still require some rigid material housing the main circuitry of the device and the oximetry sensor.

In still further embodiments, the device may have a wrist cuff and a flexible cord or wire connecting the optical sensor on the thumb. The cord or wire could connect the oximetry sensor to the main circuitry in the wrist cuff, similar to other embodiments. The wrist cuff would have to fully enclose the patient's wrist, since it is no longer held in place by the rigidity of the form factor. In this sense, it would need a fastening mechanism (i.e. Velcro, magnet) to hold the cuff close around the patient's wrist.

In other embodiments the exterior electrodes could be positioned to facilitate making contact with other parts of the body to obtain the same measurements. For example, the exterior electrodes could be pressed against the patient's chest. In other embodiments, the electrodes could be constructed with another conductive material other than foam or inflatable rubber covered in conductive fabrics. Such materials include stainless steel, transparent conductive film, rubber, copper, silver, tungsten, aluminum, zinc, iron, platinum, tin, lead, titanium, carbon steel. Both the electrodes on the wrist and the exterior electrodes can be made of a variety of conductive materials, however, flexible and forgiving materials provide adaptability for patients of varying wrist size such that the electrodes still make consistent, firm contact with the patient's skin.

In other embodiments, the handheld device described above can integrate with a 'patch' that directly adheres to a portion of a patient's body, or a 'necklace' that drapes around the patient's neck. The patch would be similar in form to the necklace's base, although it may take on other shapes and form factors. It would include most or all of the same sensors (e.g. sensors for measuring ECG, TBI, and PPG waveforms) and computing systems (e.g. microprocessors operating algorithms for processing these waveforms to determine parameters such as HR, HRV, RR, BP, SpO2, TEMP, CO, SV, fluids) as the base of the necklace. However unlike the system described above, the battery to power the patch would be located in or proximal to the base, as opposed to the strands in the case of the necklace. Also, in embodiments, the patch would include a mechanism such as a button or tab functioning as an on/off switch. Alternatively, the patch would power on when sensors therein (e.g. ECG or temperature sensors) detect that it is attached to a patient.

In typical embodiments, the patch includes a reusable electronics module (shaped, e.g., like the base of the necklace) that snaps into a disposable component that includes electrodes similar to those described above. The patch may also include openings for optical and temperature sensors as described above. In embodiments, for example, the disposable component can be a single disposable component that receives the reusable electronics module. In other embodiments, the reusable electronics module can include a reusable electrode (made, e.g., from a conductive fabric or elastomer), and the disposable component can be a simple adhesive component that adheres the reusable electrode to the patient.

In preferred embodiments the patch is worn on the chest, and thus includes both rigid and flexible circuitry, as described above. In other embodiments, the patch only includes rigid circuitry and is designed to fit on other portions of the patient's body that is more flat (e.g. the shoulder).

In embodiments, for example, the system described above can calibrate the patch or necklace for future use. For example, the handheld device can determine a patient-specific relationship between transit time and blood pressure, along with initial values of SYS, DIA, and MAP. Collectively these parameters represent a cuff-based calibration for blood pressure, which can be used by the patch or necklace for cuffless measurements of blood pressure. In other embodiments, the handheld device can measure a full-body impedance measurement and weight. These parameters can be wirelessly transmitted to the necklace or patch, where they are used with their impedance measurement to estimate full-body impedance (e.g. during a dialysis session). Additionally, during the dialysis session, the necklace or patch can use the values of full-body impedance and weight to estimate a progression towards the patient's dry weight.

These and other embodiments of the invention are deemed to be within the scope of the following claims.

What is claimed is:

1. A biometric sensor configured to measure a blood pressure value from a patient, comprising:
    an arm-receiving portion comprising a first opening configured to receive a distal portion of one of the patient's arms and a first electrode comprising a conductive material disposed on a first inflatable bladder and configured and arranged to contact the distal portion of said one of the patient's arms when said one of the patient's arms is inserted in the first opening, wherein the arm-receiving portion comprises first and second spaced-apart wall portions that extend from a body-contacting portion and form the first opening and are arranged so as to be located on opposite sides of said one of the patient's arms when said one of the patient's arms is inserted in the first opening;
    a pressure-control system comprising a pump, a valve, and a pressure sensor connected to the first inflatable bladder, the pressure-control system being configured to inflate and deflate the first inflatable bladder in response to computer commands;
    a finger-receiving portion comprising a second opening, configured and arranged to receive a finger of said one of the patient's arms while the distal portion thereof is received by the arm-receiving portion, and an optical sensor comprising a first light source configured to irradiate the finger, a photodetector configured to receive radiation after the first light source irradiates the finger, and a processing component configured to receive signals from the photodetector and to process the signals from the photodetector to generate a photoplethysmogram waveform comprising pulsatile signals;
    the body-contacting portion comprising an exterior-facing surface and a second electrode configured and arranged to contact a body location that is one of the patient's torso, legs, opposing arm, and neck when the body-contacting portion is pressed against a second body location while said one of the patient's arms is inserted in the first opening;
    an electrocardiogram (ECG) sensor comprising an ECG-measuring electrical circuit in electrical contact with the first electrode and the second electrode so that bioelectric signals pass from both the first electrode and the second electrode to the electrical circuit, which then processes the bioelectric signals to generate an ECG waveform;
    a pressure-measuring sensor comprising pressure-measuring electronics coupled to the first inflatable bladder and configured sense a pressure within the first inflatable bladder and in response generate a pressure signal representative of the sensed pressure; and
    a processing system configured to issue computer commands to the pressure-control system to inflate and deflate the first inflatable bladder while the optical sensor generates the photoplethysmogram waveform, and further configured to analyze modulations in a digital version of the photoplethysmogram waveform and a digital version of the pressure signal to estimate the blood pressure value.

2. The biometric sensor of claim 1, wherein the processing system comprises a microprocessor configured to analyze an amplitude and a pressure corresponding to at least one of the pulsatile signals.

3. The biometric sensor of claim 2, wherein the microprocessor is further configured to analyze sets of amplitudes and pressure values corresponding to a set of pulsatile signals.

4. The biometric sensor of claim 3, wherein the microprocessor is further configured to approximate amplitude values in the sets of amplitudes using a mathematical function.

5. The biometric sensor of claim 4, wherein the microprocessor is further configured to estimate systolic blood pressure ('SYS') from a minimum value of the mathematical function.

6. The biometric sensor of claim 1, wherein the arm-receiving portion further includes a second inflatable bladder which opposes the first inflatable bladder across the opening.

7. The biometric sensor of claim 6, wherein the conductive material comprised by the first electrode is a conductive, elastomeric material disposed over a surface of the first inflatable bladder.

8. The biometric sensor of claim 1, wherein the first inflatable bladder is formed from an inelastic material.

9. The biometric sensor of claim 1, wherein the conductive material comprised by the first electrode is one of a conductive fabric, a metal component, a conductive foam, a conductive polymeric material, and a hydrogel material.

10. The biometric sensor of claim 1, wherein the first electrode is disposed on a top surface of the first inflatable bladder.

11. The biometric sensor of claim 1, further comprising a circuit board disposed within the biometric sensor.

12. The biometric sensor of claim 11, wherein the ECG sensor, pressure-measuring sensor, the optical sensor, and the processing system are disposed on the circuit board.

13. The biometric sensor of claim 12 wherein the first and second electrodes are in electrical, signal-conducting contact with the ECG sensor.

14. The biometric sensor of claim 1, wherein the ECG waveform comprises a set of heartbeat-induced QRS complexes, and the processing system includes a microprocessor configured to calculate a time difference between the QRS complexes to determine the patient's heart rate.

\* \* \* \* \*